United States Patent
Lin et al.

(10) Patent No.: US 8,889,626 B2
(45) Date of Patent: Nov. 18, 2014

(54) TRIPLE CROSS-LINKED COLLAGEN, METHOD OF MANUFACTURING THE SAME, AND USE THEREOF

(75) Inventors: Yu Te Lin, Tainan (TW); Chien Hsin Lin, Tainan (TW); Hsiang Yin Lu, Pingtung (TW); Feng Huei Lin, Taipei (TW)

(73) Assignee: Sunmax Biotechnology Co., Ltd., Tainan County (TW)

( * ) Notice: Subject to any disclaimer, the term of this patent is extended or adjusted under 35 U.S.C. 154(b) by 181 days.

(21) Appl. No.: 13/443,115

(22) Filed: Apr. 10, 2012

(65) Prior Publication Data

US 2013/0039878 A1 Feb. 14, 2013

(30) Foreign Application Priority Data

Aug. 9, 2011 (TW) .............................. 100128378 A

(51) Int. Cl.
| | | |
|---|---|---|
| *A61K 38/39* | (2006.01) | |
| *A61K 31/787* | (2006.01) | |
| *C07K 14/78* | (2006.01) | |
| *C08H 1/00* | (2006.01) | |
| *C08H 1/02* | (2006.01) | |
| *A61K 38/00* | (2006.01) | |

(52) U.S. Cl.
CPC ................ *A61K 31/787* (2013.01); *C07K 14/78* (2013.01); *C08H 1/00* (2013.01); *C08H 1/02* (2013.01); *A61K 38/00* (2013.01)
USPC .......................................... 514/17.2; 530/356

(58) Field of Classification Search
CPC ......... A61K 8/65; A61K 38/39; A61K 35/35; A61K 38/014; A61K 38/00; C07K 14/78
See application file for complete search history.

(56) References Cited

FOREIGN PATENT DOCUMENTS

| CN | 101157719 A | 4/2008 |
|---|---|---|
| CN | 101648989 A | 2/2010 |
| WO | 2010021738 A2 | 2/2010 |

OTHER PUBLICATIONS

Zeeman et al., "Successive epoxy and carbodiimide cross-linking of dermal sheep collagen", Biomaterials, 1999, pp. 921-931.*
Cuiyun Li, Yang Liu, Research Progression of Chemical Cross-linking Techniques of Collagen, Chongqing Medicine, 2010, p. 2790-2792, vol. 39, No. 20, China.
Zeeman et al., "Cross-Linking of Collagen-Based Materials", Cell Biology and Biomaterials, 1998, pp. 9-17, 35-51 and 91-109, dissertation.
Dan Nianhua, Dan Weihua, Zeng Rui, Mi Zhenjian, Lin Hai, Chen Chi, Qu Jianjian, Ye Yichun, Guan Linbo, "Application of Epoxy Compound in Collagen Modification", China Academic Journal Electronic Publishing House, Jun. 2006, vol. 20, No. 6, pp. 119-122.

* cited by examiner

Primary Examiner — Karlheinz R Skowronek
Assistant Examiner — Lianko Garyu
(74) Attorney, Agent, or Firm — Bacon & Thomas, PLLC

(57) ABSTRACT

The present invention relates to a method for manufacturing a triple cross-linked collagen, which comprises the following steps: providing a soluble collagen sample; mixing the collagen sample with a first cross-linking agent to form a one cross-linked collagen; mixing the first cross-linked collagen with a second cross-linking agent to form a second cross-linked collagen; and mixing the second cross-linked collagen with a third cross-linking agent to form a triple cross-linked collagen, wherein each of the first cross-linking agent, the second cross-linking agent, and the third cross-linking agent is selected from the group consisting of an aldehyde cross-linking agent, an imine cross-linking agent, and an epoxide cross-linking agent. In addition, the first cross-linking agent is different form the second cross-linking agent, and the third cross-linking agent is different form the first cross-linking agent and the second cross-linking agent.

20 Claims, 3 Drawing Sheets

TRIPLE CROSS-LINKED COLLAGEN, METHOD OF MANUFACTURING THE SAME, AND USE THEREOF

CROSS REFERENCE TO RELATED APPLICATION

This application claims the benefits of Taiwan Patent Application Serial Number 100128378, filed on Aug. 9, 2011, the subject matter of which is incorporated herein by reference.

BACKGROUND OF THE INVENTION

1. Field of the Invention

The present invention relates to a method of manufacturing a triple cross-linked collagen. More specifically, the present invention relates to a method of manufacturing a triple cross-linked collagen with high melting point, low ratio of enzyme degradation, and high stability. The triple cross-linked collagen of the present invention can further be applied to long-term implant medical treatment.

2. Description of Related Art

Collagen can be widely found in the connective tissue, and collagen is also the elementary matrix for various human tissues such as bones, cartilages, ligaments, tendons, vessels, cornea, basement membranes, and skins. Moreover, because of the low immunological reactivity of collagen, collagen is widely applied in medical composition for treatment or tissue engineering to enhance the strength of tissues or to protect tissues.

However, it is found that many medical implants simply made of collagen-based materials are generally degraded in the body in a short time. Hence, most of the modern medical implants are made of cross-linked collagen with improved and stable structure instead of pure collagen.

Currently, the cross-linked collagen is made through either physical cross-linking reaction or chemical cross-linking reaction. Most of the time, physical cross-linking reaction for collagen is achieved by way of radioisotopes, UV radiation, or thermal dehydration. However, the cross-linked collagen obtained through physical cross-linking is apt to be destroyed, denatured, or degraded. Hence, physical cross-linking reaction is not a suitable method for manufacturing collagen for medical applications. On the other hand, the chemical cross-linking reaction of collagen is achieved through the application of cross-linking agent. is used to obtain the chemical cross-linking reaction. However, most of the residual cross-linking agents applied in the chemical cross-linking reaction for manufacturing cross-linked collagen is toxic for human body. In addition, owing to the disadvantages such as low melting point, and a high ratio of enzyme degradation, the cross-linked collagen manufactured by chemical cross-linking reaction hence is further limited to the application for temporary implants or very specific medical treatments. In fact, even though there are both amino functional groups and carboxylic functional groups in the collagen molecules, only the amino functional groups inside or between the collagen molecules react with each other in most chemical cross-linking reactions. Thus, uneven cross-linked collagen with low degree of cross-linking is frequently obtained through these chemical cross-linking reactions. Therefore, the resistance against enzyme degradation cannot be effectively improved.

In view of improving the problems illustrated above, a method of manufacturing a collagen with high degree of cross-linking to lower the rate of degradation, enhance the stability of collagen, and provide more choices for medical material is in strong demand.

SUMMARY OF THE INVENTION

The object of the present invention is to provide a method of manufacturing a triple cross-linked collagen with high degree of cross-linking, high melting point, low enzyme degradation, and enhanced stability.

Another object of the present invention is to provide a triple cross-linked collagen composition with enhanced stability, high melting point, and low enzyme degradation.

To achieve the object, the present invention provides a method of manufacturing a triple cross-linked collagen, which comprises the following steps: providing a soluble collagen sample; mixing the collagen sample with a first cross-linking agent to form a first cross-linked collagen; mixing the first cross-linked collagen with a second cross-linking agent to form a second cross-linked collagen; mixing the second cross-linked collagen with a third cross-linking agent to form a triple cross-linked collagen. The first cross-linking agent is one selected from the group consisting of an aldehyde cross-linking agent, an imine cross-linking agent, and an epoxide cross-linking agent. The second cross-linking agent is one selected from the group consisting of an aldehyde cross-linking agent, an imine cross-linking agent, and an epoxide cross-linking agent, and the second cross-linking agent is different from the first cross-linking agent. In addition, the third cross-linking agent is one selected from the group of consisting an aldehyde cross-linking agent, an imine cross-linking agent, and an epoxide cross-linking agent, and the third cross-linking agent is different from the first cross-linking agent and the second cross-linking agent. Therefore, the first cross-linking agent, the second cross-linking agent, and the third cross-linking agent are different from each other.

In addition, the aforementioned method can further comprise a step after forming the triple cross-linked collagen: mixing the triple cross-linked collagen with an excessive glycine solution, and washing the triple cross-linked collagen by a phosphate buffer to neutralize the triple cross-linked collagen.

The degree of cross-linking of the triple cross-linked collagen by the above method can be 70-90%, the melting point of the triple cross-linked collagen can be 80-95° C., and the ratio of enzyme degradation of the triple cross-linked collagen can be 10% or less.

The aldehyde cross-linking agent of the present invention is not particularly limited. Preferably, the aldehyde cross-linking agent is at least one selected from the group consisting of: formaldehyde, glyoxal, and glutaraldehyde. More preferably, the aldehyde cross-linking agent is formaldehyde. The aldehyde cross-linking agent may induce inter- and intra-molecular cross-linking reaction between amino groups of collagens. Hence, covalent bonds may be formed between the amino groups of collagens through the assistance of aldehyde cross-linking agents. In addition, the aldehyde cross-linking agent reacts in acidic environment. Preferably, the aldehyde cross-linking agent reacts in pH 6 to pH 9. More preferably, the aldehyde cross-linking agent reacts in pH 6.5 to pH 7.5. Most preferably, the aldehyde cross-linking agent reacts in pH 6.8 to pH 7.3. Furthermore, when the aldehyde cross-linking agent is used, the reaction temperature of the cross-linking reaction is not limited, as long as the collagen does not denature. Preferably, the temperature of the cross-linking reaction is 20° C. to 50° C. More preferably, the temperature of the cross-linking reaction is 25° C. to 40° C. Most preferably, the temperature of the cross-linking reaction is 28° C. to 35° C. In addition, the concentration of the aldehyde cross-linking agent for the cross-linking reaction is also not limited, as long as the aldehyde cross-linking agent can induce the inter- and intra-molecular cross-linking reaction between amino groups of collagens. Preferably, the concentration of the aldehyde cross-linking agent is 15 ppm to 70 ppm. More preferably, the concentration of the aldehyde cross-linking agent is 25 ppm to 50 ppm. Most preferably, the concentration of the aldehyde cross-linking agent is 30 ppm to 40 ppm.

The aforementioned imine cross-linking agent of the present invention is not particularly limited. Preferably, the imine cross-linking agent of the present invention is at least one selected from the group consisting of 1-ethyl-3-(3-dimethylaminopropyl)carbodiimide hydrochloride (EDC), 1-Cyclohexyl-3-(2-morpholinoethyl)carbodiimide (CMC), dicyclohexyl carbodiimide (DCC), and diisopropyl carbodiimide (DIC). More preferably, the imine cross-linking agent of the present invention is 1-ethyl-3-(3-dimethylaminopropyl)carbodiimide hydrochloride (EDC). The imine cross-linking agent of the present invention can induce inter- and intra-molecular cross-linking reaction between amine groups of collagen. In addition, the imine cross-linking agent can further comprise N-hydroxysuccinimide (NHS) to form a mixture of imine cross-linking agent (EDC/NHS), wherein the molar ratio of EDC and NHS is not particularly limited. Preferably, the molar ratio of EDC and NHS is about 1:2, 2:1, 5:1, or 5:2. More preferably, the molar ratio of EDC and NHS is about 2:1, 5:1, or 5:2. Most preferably, the molar ratio of EDC and NHS is 5:1. Furthermore, the imine cross-linking agent of the present invention can react in an acidic environment. Preferably, the imine cross-linking agent reacts in pH 4 to pH 6. More preferably, the imine cross-linking agent reacts in pH 4.5 to pH 5.8. Most preferably, the imine cross-linking agent reacts in pH 5.2 to pH 5.7. When the imine cross-linking agent is used, the temperature of cross-linking reaction is not specially limited, as long as the collagen does not denature. Preferably, the temperature of the cross-linking reaction is 30° C. to 50° C. More preferably, the temperature of the cross-linking reaction is 35° C. to 45° C. Most preferably, the temperature of the cross-linking reaction is 38° C. to 42° C. Moreover, the concentration of the imine cross-linking agent for the cross-linking reaction is not limited, as long as the imine cross-linking agent can induce inter- and intra-molecular cross-linking reaction between amine groups of collagen. Preferably, the volume percentage concentration of the imine cross-linking agent is about 0.5% to 5%. More preferably, the volume percentage concentration of the imine cross-linking agent is about 1% to 4%. Most preferably, the volume percentage concentration of the imine cross-linking agent is about 1% to 3%.

In addition, the aforementioned epoxide cross-linking agent of the present invention is not limited. Preferably, the epoxide cross-linking agent of the present invention is one selected from the group of 1,4-butanediol diglycidyl ether (BDDE), ethylene glycol diglycidyl ether (EGDGE), glycerol polyglycidyl ether, and diglycerol polyglycidyl ether. More preferably, the epoxide cross-linking agent is 1,4-butanediol diglycidyl ether (BDDE) and ethylene glycol diglycidyl ether (EGDGE). Most preferably, the epoxide cross-linking agent is 1,4-butanediol diglycidyl ether (BDDE). The epoxide cross-linking agent can induce inter- and intra-molecular cross-linking reaction between amine groups of collagen in an alkaline environment; however, the epoxide cross-linking agent can induce inter- and intra-molecular cross-linking reaction between carboxylic groups of collagen in an acidic environment. Hence, in the present invention, the epoxide cross-linking agent can induce inter- and intra-molecular cross-linking reaction between carboxylic groups of collagen in an acidic environment. Preferably, the epoxide cross-linking agent of the present invention reacts in pH 3 to pH 5. More preferably, the epoxide cross-linking agent of the present invention reacts in pH 4 to pH 4.8. Most preferably, the epoxide cross-linking agent of the present invention reacts in pH 4.3 to pH 4.7. The temperature of the epoxide cross-linking agent for the present invention is also not limited, as long as the collagen does not denature. Preferably, the temperature of cross-linking reaction is 30° C. to 50° C. More preferably, the temperature of cross-linking reaction is 35° C. to 45° C. Most preferably, the temperature of cross-linking reaction is 38° C. to 43° C. Furthermore, the concentration of the epoxide cross-linking agent for the cross-linking reaction is also not limited, as long as the epoxide cross-linking agent can induce inter- and intra-molecular cross-linking reaction between carboxylic groups of collagen. Preferably, the volume percentage concentration of the epoxide cross-linking agent is about 0.5% to 4%. More preferably, the volume percentage concentration of the epoxide cross-linking agent is about 1% to 3%. Most preferably, the volume percentage concentration of the epoxide cross-linking agent is about 1% to 2.5%.

Preferably, in the present invention, the first cross-linking agent can induce inter- and intra-molecular cross-linking reaction between amino groups of collagen. Therefore, in the present invention, the first cross-linking agent is the aldehyde cross-linking agent or the epoxide cross-linking agent, wherein the epoxide cross-linking agent can induce inter- and intra-molecular cross-linking reaction between amino groups of collagen in an alkaline environment. More preferably, the first cross-linking agent in the present invention is the aldehyde cross-linking agent. Most preferably, the first cross-linking agent in the present invention is glutaraldehyde.

The aforementioned collagen sample of the present invention can comprise a collagen fiber, wherein the collagen sample is preferably at least one selected from the group consisting of bovine collagen, swine collagen, sheep collagen, horse collagen, fish collagen, and human collagen. In addition, the collagen sample is at least one selected from the group consisting of type I collagen, type II collagen, type III collagen, type IV collagen, and type V collagen. Preferably, the collagen sample is type I collagen and type II collagen. More preferably, the collagen sample is type I collagen. Furthermore, the collagen sample of the present invention can also be a recombinant collagen fiber, wherein the collagen sample can participate in the cross-linking reaction with the cross-linking agent by forming covalent bonds.

The aforementioned other object of the present invention is to provide a triple cross-linked collagen composition, comprising: a triple cross-linked collagen and a carrier, wherein the triple cross-linking collagen is manufactured by the aforementioned method of the present invention. The degree of cross-linking of the triple cross-linked collagen is 70-90%, the melting point of the triple cross-linked collagen is 80-95° C., and the ratio of enzyme degradation of the triple cross-linked collagen is 10% or less. In addition, the carrier can comprise methylcellulose, ethylcellulose, carboxymethyl cellulose acetate ester phthalates ester, complex of hydroxypropyl cellulose and hydroxypropyl methylcellulose, polyethylene chloride, polyethylene, polyvinyl pyrrolidone, stearyl alcohol, glyceryl monostearate, Polyisobutylene acid ester, polymethacrylic acid ester, polyethylene glycol, hydrophilic gel, and so on. Furthermore, the triple cross-linked collagen composition can further comprise antioxidants, gelling agents, stabilizers, excipients, surfactants, or a combination thereof, in order to form a collagen material with high biocompatibility and suitable for long-term medical implantation. The application of the triple cross-linked collagen composition is not limited. Preferably, the triple cross-linked collagen can be applied in dentistry, orthopedics, neurosurgery, plastic surgery, or used as pharmaceutical carriers. According to the application of the triple cross-linked collagen, the triple cross-linked collagen may be used as microplastic surgery implant, bone repair material, artificial skin, cartilage improvement, or a pharmaceutical carrier with drug release controlled property.

DETAILED DESCRIPTION OF THE PREFERRED EMBODIMENT

Figure 1:
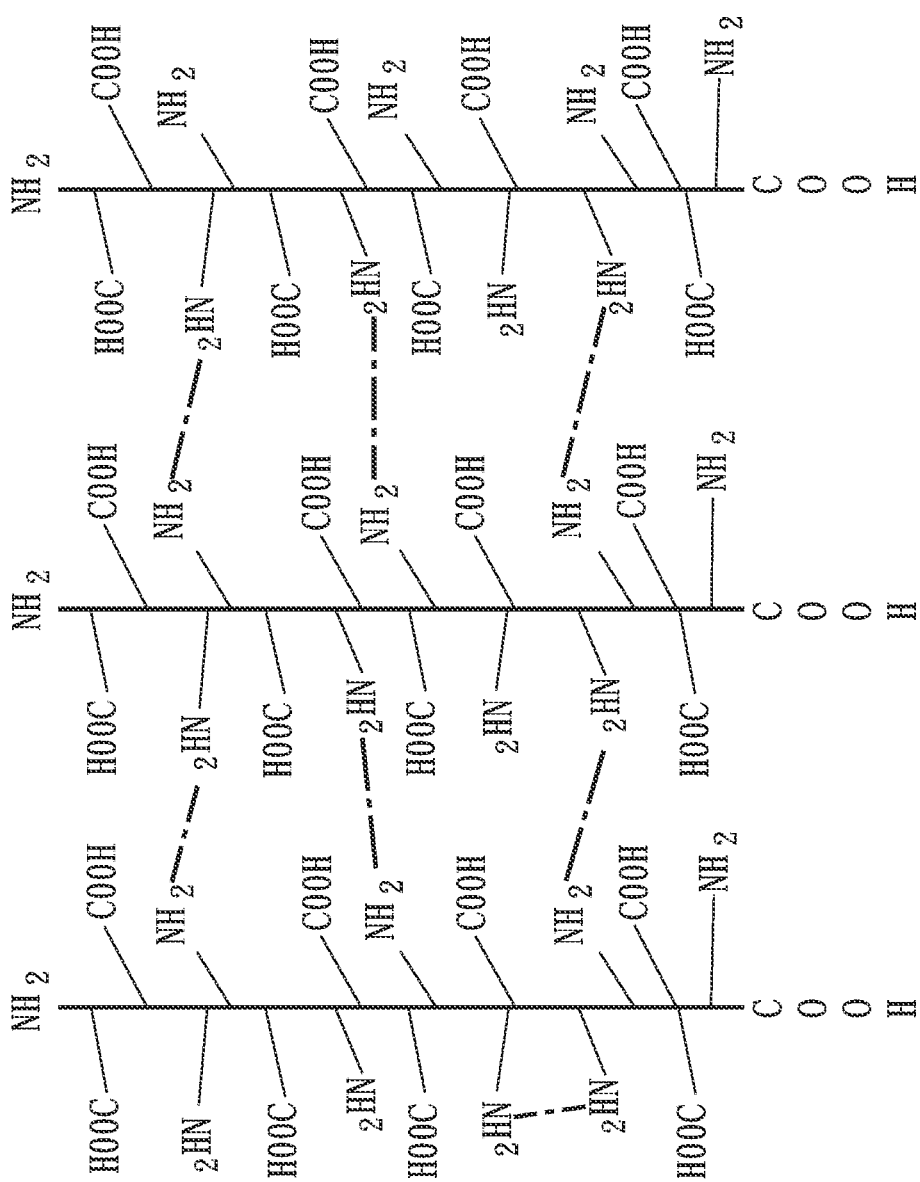
FIG. 1 is a perspective view showing the structure of a first cross-linked collagen according to Comparative example 1.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Example 1

1-1 Preparation of the Recombinant Collagen Fibers

In the present example, the collagen fibers were extracted from the pigskin to obtain a swine collagen fiber solution. The collagen solution and a phosphate buffer (0.2 M, pH 11.2) were mixed and stirred slowly at 25° C. for 6 hours to perform a recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the obtained recombinant collagen fibers were suspended in a phosphate buffer (20 mM, pH 7) to obtain the recombinant collagen fibers solution (2.7 mg/ml).

1-2 Preparation of the First Cross-Linked Collagen Fibers

In the present example, the first cross-linking agent is glutaraldehyde, which is one kind of aldehyde cross-linking agent. The recombinant fibers solution (2.7 mg/ml) and glutaraldehyde were mixed and stirred slowly at 30° C., pH 7.2, for 16 hours to perform the first cross-linking reaction, in which the inter- and intra-molecular amino groups of collagen fibers were cross-linked with each other. In the first cross-linking reaction, the final concentration of glutaraldehyde is 35 ppm. After the first cross-linking reaction was finished, the first cross-linked collagen fibers were collected by centrifugation to obtain the product of the present example.

1-3 Preparation of Second Cross-Linked Fibers

In the present example, the second cross-linking agent was 1,4-butanediol diglycidyl ether (BDDE), which is the epoxide cross-linking agent. The first cross-linked collagen fibers were suspended in a phosphate buffer (20 mM, pH 4.5) to obtain the first cross-linked collagen solution (2.7 mg/ml). Then, the first cross-linked collagen solution (2.7 mg/ml) and BDDE were mixed and stirred slowly at 40° C., pH 4.5, for 16 hours to perform the second cross-linking reaction. In the second cross-linking reaction, the final volume percentage concentration of BDDE is 1%. After the second cross-linking reaction was finished, the second cross-linked collagen fibers were collected by centrifugation.

In the present example of the second cross-linking reaction, the second cross-linking agent induced the second cross-linking reaction in an acidic environment. Therefore, the second cross-linking agent induced inter- and intra-molecular cross-linking reaction between carboxylic groups of the first cross-linked collagen fibers.

1-4 Preparation of the Triple Cross-Linked Fibers

The third cross-linking agent used in the present example comprised 1-ethyl-3-(3 dimethylaminopropyl)carbodiimide hydrochloride (EDC), which was the imine cross-linking agent. In addition, the third cross-linking agent further comprised N-hydroxysuccinimide (NHS) to form a mixture of the third cross-linking agent (EDC/NHS), which was the third cross-linking agent of the present example. In the third cross-linking agent, the molar ratio of EDC and NHS was 5:1.

The second cross-linked collagen fibers were suspended in a MES buffer (0.1 M, pH 5.5) to obtain the second cross-linked collagen solution (2.7 mg/ml). Then, the third cross-linking agent (EDC/NHS) and the second cross-linked collagen solution (2.7 mg/ml) were mixed and stirred slowly at 40° C., pH 5.5, for 16 hours to perform the third cross-linking reaction, in which the inter- and intra-molecular amino group and carboxylic group of collagen fibers were cross-linked with each other. In the third cross-linking reaction, the final volume percentage concentration of EDC was 1%. After the third cross-linking reaction was finished, the third cross-linked collagen fibers were collected by centrifugation. The collected third cross-linked collagen fibers were added to glycine solution (0.1 M) and stirred slowly for 6 hours, in which the volume of the glycine solution was 10 times the volume of the triple cross-linked collagen fibers. Then, the triple cross-linked collagen fibers were collected again by centrifugation.

After the collection, the triple cross-linked collagen fibers were washed three times by a phosphate buffer (pH 7), in which the volume of the phosphate buffer was 10 times the volume of the triple cross-linked collagen fibers. Finally, the triple cross-linked collagen fibers were collected by centrifugation to obtain the product of the present embodiment.

Test Example 1

1-1 Detect the Degree of Cross-Linking

In the present test example, trinitrobenzenesulphonate (TNBS) agent was used for analyzing the degree of cross-linking of the triple cross-linked collagen, which was manufactured by example 1.

<Test 1>

4 mg freeze-dried triple cross-linked collagen fibers were added into 1 ml sodium bicarbonate solution (0.1 M, pH 8.5).

Then, 1 ml TNBS (volume percentage concentration is 0.5%) was added into the sodium bicarbonate solution to react at 40° C. for 2 hours. After the reaction was finished, 3 ml HCl (6 N) was further added to react again at 60° C. for 1.5 hours. When the reaction was finished and the reacted solution was cooled down to room temperature, 5 ml de-ionized water was added and mixed evenly to the reacted solution. Then, 5 ml of the reacted solution mixed with de-ionized water was used and mixed with 10 ml ether in a spiral tube, in which the ether mixed solution in the spiral tube was shaken to mix evenly. Subsequently, the solution in the spiral tube was left standing to separate into layers. When the formation of layers was finished, the upper layer of ether was removed. After ether was added in and removed from the reacted solution in the spiral tube three times as in the above steps, 400 μl of the reacted solution was used and mixed evenly with 800 μl de-ionized water (the volume ratio of the reacted solution:the volume ratio of water is 1:2), in which the ether was vaporized from the reacted solution. Afterward, the solution (400 μl of the reacted solution with 800 μl de-ionized water) was analyzed by using a wavelength of 345 nm to obtain the absorbance value of the triple cross-linked collagen, and the degree of cross-linking of the triple cross-linked collagen was calculated by the formula described below.

<Test 2>

The steps of the present test were roughly the same as those of test 1. The only difference between the present test and test 1 was the sample used. The sample used in the present test was the freeze-dried collagen without proceeding the cross-linking reaction.

<Comparative Test>

The steps of the present test were roughly the same as those of test 1. The only difference of the present comparative test and test 1 was the sample used. The sample used in the present comparative test was not the freeze-dried triple cross-linked collagen, but water.

The formula for calculating the degree of cross-linking:

$$\text{The degree of cross-linking}(\%) = \frac{[A - B]}{A} * 100$$

A=(the absorbance value of test 2)−(the absorbance value of the comparative test)
B=(the absorbance value of test 1)−(the absorbance value of the comparative test)

1-2 Detection of the Ratio of Enzyme Degradation 1 g freeze-dried triple cross-linked collagen was added in 0.1 ml collagen enzyme solution (0.5 unit/ml, 50 mM TES+ 0.36 mM $CaCl_2 \cdot 2H_2O$, pH 7.4) to react at 37° C. for 24 hr. When the reaction was finished, 0.2 ml supernatant was collected by centrifugation (10000 rpm, 10 min). Then, 1 ml ninhydrin was added into the supernatant to react at 100° C. for 20 min. After the reaction was finished and cooled down to room temperature, the reacted solution was analyzed by an equipment using a wavelength of 570 nm. to obtain the absorbance value of the solution.

Figure 3:
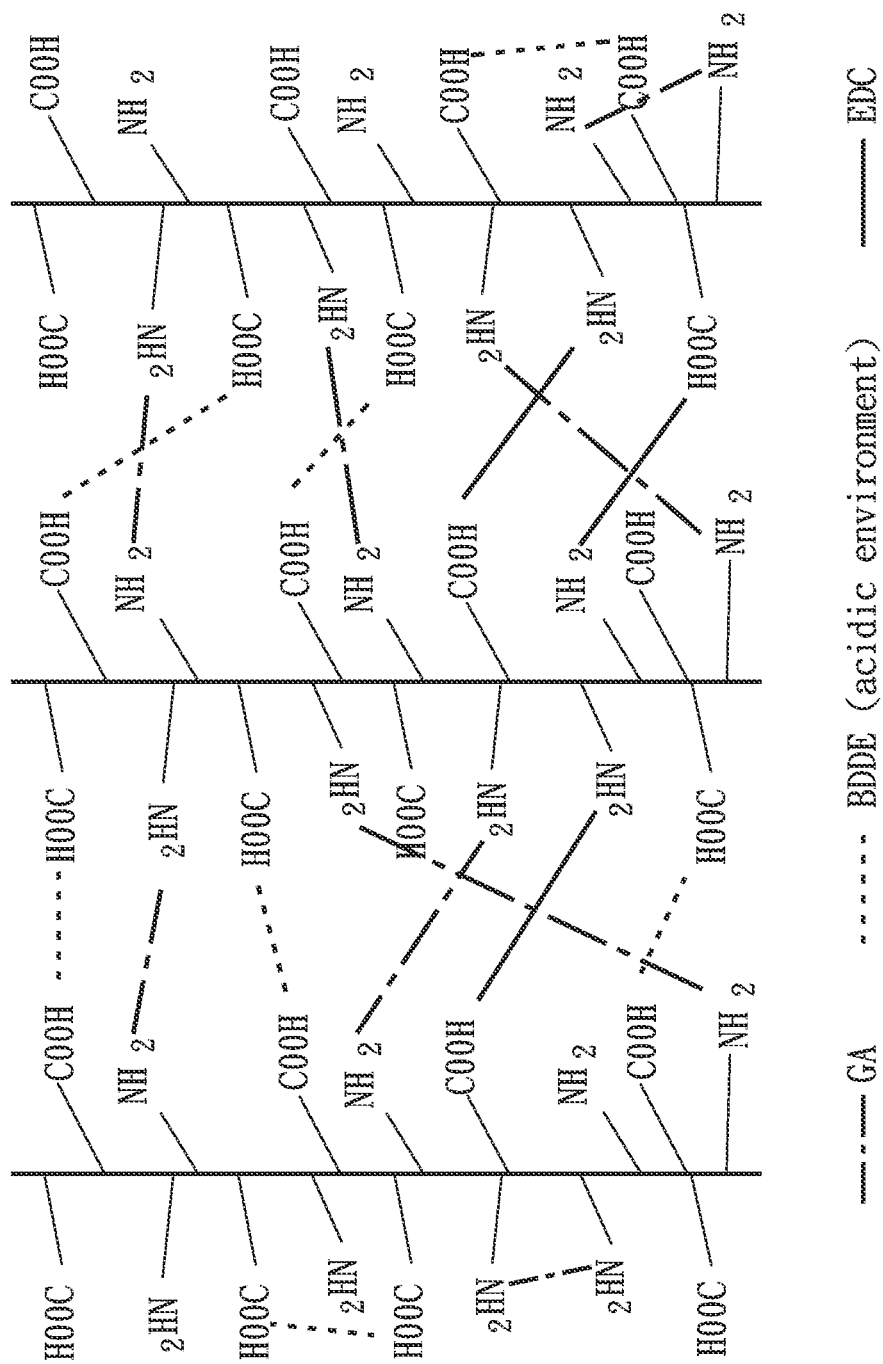
FIG. 3 is a perspective view showing the structure of a triple cross-linked collagen according to the present invention.

Finally, the result of the present example is shown in table 1 and FIG. 3, which is a perspective view showing the structure of a triple cross-linked collagen according to the present invention. According to the result of the present example in table 1, the productivity of the triple cross-linked collagen was 83%, the degree of cross-linking of the triple cross-linked collagen was 75.62%, the melting point of the triple cross-linked collagen was 82.18° C., and the ratio of enzyme degradation of the triple cross-linked collagen was 9.17%.

Example 2

2-1 Preparation of the Recombinant Collagen Fibers

The steps for preparing the recombinant collagen fibers were the same as the steps of example 1.

2-2 Preparation of the First Cross-Linked Fibers

The steps for preparing the first cross-linked collagen fibers were the same as the steps of example 1.

2-3 Preparation of the Second Cross-Linked Fibers

The second cross-linking agent used in the present example comprised 1-ethyl-3-(3 dimethylaminopropyl)carbodiimide hydrochloride (EDC), which was the imine cross-linking agent. In addition, the second cross-linking agent further comprised N-hydroxysuccinimide (NHS) to form a mixture of the second cross-linking agent (EDC/NHS), which was the second cross-linking agent of the present example. In the second cross-linking agent, the molar ratio of EDC and NHS was 5:1. The first cross-linked collagen fibers were suspended in the in a MES buffer (0.1 M, pH 5.5) to obtain the first cross-linked collagen solution (2.7 mg/ml). Then, the second cross-linking agent (EDC/NHS) and the first cross-linked collagen solution (2.7 mg/ml) were mixed and stirred slowly at 40° C., pH 5.5, for 16 hours to perform the second cross-linking reaction, in which the inter- and intra-molecular amino group and carboxylic group of collagen fibers were cross-linked with each other. In the second cross-linking reaction, the final volume percentage concentration of EDC was 1%. After the second cross-linking reaction was finished, the second cross-linked collagen fibers were collected by centrifugation to obtain the product of the present example.

2-4 Preparation of the Triple Cross-Linked Fibers

In the present example, the third cross-linking agent was 1,4-butanediol diglycidyl ether (BDDE), which is the epoxide cross-linking agent. The second cross-linked collagen fibers were suspended in a phosphate buffer (20 mM, pH 4.5) to obtain the second cross-linked collagen solution (2.7 mg/ml). Then, the second cross-linked collagen solution (2.7 mg/ml) and BDDE were mixed and stirred slowly at 40° C., pH 4.5, for 16 hours to perform the third cross-linking reaction, in which the inter- and intra-molecular carboxylic group and carboxylic group of collagen fibers were cross-linked with each other. In the third cross-linking reaction, the final volume percentage concentration of BDDE is 1%. After the third cross-linking reaction was finished, the triple cross-linked collagen fibers were collected by centrifugation. The collected third cross-linked collagen fibers were added to glycine solution (0.1 M) and stirred slowly for 6 hours, in which the volume of the glycine solution was 10 times the volume of the triple cross-linked collagen fibers. Then, the triple cross-linked collagen fibers were collected again by centrifugation.

After the collection, the triple cross-linked collagen fibers were washed three times by the phosphate buffer (pH 7), in which the volume of the phosphate buffer was 10 times the volume of the third cross-linked collagen fibers. Finally, the triple cross-linked collagen fibers were collected by centrifugation to obtain the product of the present embodiment.

Finally, the result of the present example is shown in table 1. According to the result of the present example in table 1, the productivity of the triple cross-linked collagen was 77%, the degree of cross-linking of the triple cross-linked collagen was 76.61%, the melting point of the triple cross-linked collagen was 84.53° C., and the ratio of enzyme degradation of the triple cross-linked collagen was 8.34%.

Example 3

3-1 Preparation of the Recombinant Collagen Fibers

The collagen fibers were extracted from pigskin to obtain a swine collagen fiber solution. The collagen solution and the phosphate buffer (0.2 M, pH 11.2) were mixed and stirred slowly at 25° C. for 6 hours to perform the recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the recombinant collagen fibers were suspended in a MES buffer (0.1 M, pH 5.5) to obtain the recombinant collagen fibers solution (2.7 mg/ml).

3-2 Prepare First Cross-Linked Fibers

The first cross-linking agent used in the present example comprised 1-ethyl-3-(3-dimethylaminopropyl) carbodiimide hydrochloride (EDC), which was the imine cross-linking agent. In addition, the first cross-linking agent further comprised N-hydroxysuccinimide (NHS) to form a mixture of the first cross-linking agent (EDC/NHS), which was the first cross-linking agent of the present example. In the first cross-linking agent, the molar ratio of EDC and NHS was 5:1.

The first cross-linking agent (EDC/NHS) and the recombinant collagen fibers solution (2.7 mg/ml) were mixed and stirred slowly at 40° C., pH 5.5, for 16 hours to perform the first cross-linking reaction, in which the inter- and intra-molecular amino group and carboxylic group of collagen fibers were cross-linked with each other. In the first cross-linking reaction, the final volume percentage concentration of EDC was 1%. After the first cross-linking reaction was finished, the first cross-linked collagen fibers were collected by centrifugation.

The first cross-linked collagen fibers were suspended in a phosphate buffer (20 mM, pH 7) to obtain the first cross-linked collagen solution (2.7 mg/ml).

3-3 Preparation of the Second Cross-Linked Fibers

In the present example, the second cross-linking agent is glutaraldehyde, which is the aldehyde cross-linking agent. The first cross-linked collagen solution (2.7 mg/ml) and glutaraldehyde were mixed and stirred slowly at 30° C., pH 7.2, for 16 hours to perform the second cross-linking reaction, in which the inter- and intra-molecular amino groups of collagen fibers were cross-linked with each other. In the second cross-linking reaction, the final concentration of glutaraldehyde is 35 ppm. After the second cross-linking reaction was finished, the second cross-linked collagen fibers were collected by centrifugation to obtain the product of the present example.

3-4 Preparation of the Triple Cross-Linked Fibers

In the present example, the third cross-linking agent was 1,4-butanediol diglycidyl ether (BDDE), which is the epoxide cross-linking agent. The second cross-linked collagen fibers were suspended in a phosphate buffer (20 mM, pH 4.5) to obtain the second cross-linked collagen solution (2.7 mg/ml). Then, the second cross-linked collagen solution (2.7 mg/ml) and BDDE were mixed and stirred slowly at 40° C., pH 4.5, for 16 hours to perform the third cross-linking reaction, in which the inter- and intra-molecular carboxylic group and carboxylic group of collagen fibers were cross-linked with each other. In the third cross-linking reaction, the final volume percentage concentration of BDDE is 1%. After the third cross-linking reaction was finished, the triple cross-linked collagen fibers were collected by centrifugation.

The collected third cross-linked collagen fibers were added to glycine solution (0.1 M) and stirred slowly for 6 hours, in which the volume of the glycine solution was 10 times the volume of the triple cross-linked collagen fibers. Then, the triple cross-linked collagen fibers were collected again by centrifugation.

After collection, the triple cross-linked collagen fibers were washed three times by a phosphate buffer (pH 7), in which the volume of the phosphate buffer was 10 times the volume of the third cross-linked collagen fibers. Finally, the triple cross-linked collagen fibers were collected by centrifugation to obtain the product of the present embodiment.

Finally, the result of the present example is shown in table 1. According to the result of the present example in table 1, the productivity of the triple cross-linked collagen was 73.8%, the degree of cross-linking of the triple cross-linked collagen was 76.43%, the melting point of the triple cross-linked collagen was 81.75° C., and the ratio of enzyme degradation of the triple cross-linked collagen was 8.11%.

Comparative Example 1

1-1 Preparation of the Recombinant Collagen Fibers

In the present comparative example, the collagen fibers were extracted from pigskin to obtain a swine collagen fiber solution. The collagen solution and a phosphate buffer (0.2 M, pH 11.2) were mixed and stirred slowly at 25° C. for 6 hours to perform the recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the obtained recombinant collagen fibers were suspended in a phosphate buffer (20 mM, pH 7) to obtain the recombinant collagen fibers solution (2.7 mg/ml).

1-2 Preparation of the First Cross-Linked Fibers

In the present comparative example, the first cross-linking agent is glutaraldehyde, which is the aldehyde cross-linking agent. The recombinant fibers solution (2.7 mg/ml) and glutaraldehyde were mixed and stirred slowly at 30° C., pH 7.2, for 16 hours to perform the first cross-linking reaction, in which the inter- and intra-molecular amino groups of collagen fibers were cross-linked with each other. In the first cross-linking reaction, the final concentration of glutaraldehyde is 35 ppm. After the first cross-linking reaction was finished, the first cross-linked collagen fibers were collected by centrifugation to obtain the product of the present comparative example.

The collected first cross-linked collagen fibers were added to glycine solution (0.1 M) and stirred slowly for 6 hours, in which the volume of the glycine solution was 10 times the volume of the first cross-linked collagen fibers. Then, the first cross-linked collagen fibers were collected again by centrifugation.

After the collection, the first cross-linked collagen fibers were washed three times by a phosphate buffer (pH 7), in which the volume of the phosphate buffer was 10 times the volume of the first cross-linked collagen fibers. Finally, the first cross-linked collagen fibers were collected by centrifugation to obtain the product of the present comparative example.

The detection steps of the degree of cross-linking and the ratio of enzyme degradation for the cross-linked collagen of the present comparative example were the same as the test example 1. The result of the present comparative example is shown in table 1 and FIG. 1, which is a perspective view showing the structure of a first cross-linked collagen according to comparative example 1. The productivity of the cross-linked collagen in the present comparative example was 91.2%. However, the degree of cross-linking was only 32.88%, the melting point was only 68.33° C., and the ratio of enzyme degradation was 100%. Therefore, the cross-linked collagen, which was prepared by the present comparative example, has a low degree of cross-linking and high ratio of enzyme degradation compared with examples 1-3.

Comparative Example 2

2-1 Preparation of the recombinant collagen fibers

In the present comparative example, the collagen fibers were extracted from pigskin to obtain a swine collagen fiber solution. The collagen solution and a phosphate buffer (0.2 M, pH 11.2) were mixed and stirred slowly at 25° C. for 6 hours to perform the recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the obtained recombinant collagen fibers were suspended in a phosphate buffer (20 mM, pH 4.5) to obtain the recombinant collagen fibers solution (2.7 mg/ml).

2-2 Prepare First Cross-Linked Fibers

In the present comparative example, the first cross-linking agent was 1,4-butanediol diglycidyl ether (BDDE), which is the epoxide cross-linking agent. The recombinant collagen fibers solution (2.7 mg/ml) and BDDE were mixed and stirred slowly at 40° C., pH 4.5, for 16 hours to perform the first cross-linking reaction. In the first cross-linking reaction, the final volume percentage concentration of BDDE is 1%. After the first cross-linking reaction was finished, the first cross-linked collagen fibers were collected by centrifugation.

The collected first cross-linked collagen fibers were added to glycine solution (0.1 M) and stirred slowly for 6 hours, in which the volume of the glycine solution was 10 times the volume of the triple cross-linked collagen fibers. Then, the first cross-linked collagen fibers were collected again by centrifugation.

After the collection, the first cross-linked collagen fibers were washed three times by a phosphate buffer (pH 7), in which the volume of the phosphate buffer was with 10 times the volume of the first cross-linked collagen fibers. Finally, the first cross-linked collagen fibers were collected by centrifugation to obtain the product of the present comparative embodiment.

The detection steps of the degree of cross-linking and the ratio of enzyme degradation for the cross-linked collagen of the present comparative example were the same as test example 1. The result of the present comparative example is shown in table 1. The productivity of the cross-linked collagen of the present comparative example was 38.5%, the degree of cross-linking was 8.5%, the melting point was 50.33° C., and the ratio of enzyme degradation was 34%. Therefore, the productivity, the degree of cross-linking, the melting point, and the ratio of enzyme degradation of the cross-linked collagen prepared by the present comparative example were not as excellent as the examples 1 to 3.

Comparative Example 3

3-1 Preparation of the Recombinant Collagen Fibers

In the present comparative example, the collagen fibers were extracted from pigskin to obtain a swine collagen fiber solution. The collagen solution and a phosphate buffer (0.2 M, pH 11.2) were mixed and stirred slowly at 25° C. for 6 hours to perform the recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the obtained recombinant collagen fibers were suspended in a phosphate buffer (20 mM, pH 9.5) to obtain the recombinant collagen fibers solution (2.7 mg/ml).

3-2 Preparation of the First Cross-Linked Fibers

In the present comparative example, the first cross-linking agent was 1,4-butanediol diglycidyl ether (BDDE), which is the epoxide cross-linking agent. The recombinant collagen fibers solution (2.7 mg/ml) and BDDE were mixed and stirred slowly at 40° C., pH 9.5, for 16 hours to perform the first cross-linking reaction, in which the inter- and intra-molecular amino groups of collagen fibers were cross-linked with each other. In the first cross-linking reaction, the final volume percentage concentration of BDDE is 1%. After the first cross-linking reaction was finished, the first cross-linked collagen fibers were collected by centrifugation.

The collected first cross-linked collagen fibers were added to glycine solution (0.1 M) and stirred slowly for 6 hours, in which the volume of the glycine solution was 10 times the volume of the triple cross-linked collagen fibers. Then, the first cross-linked collagen fibers were collected again by centrifugation.

After the collection, the first cross-linked collagen fibers were washed three times by a phosphate buffer (pH 7), in which the volume of the phosphate buffer was 10 times the volume of the first cross-linked collagen fibers. Finally, the first cross-linked collagen fibers were collected by centrifugation to obtain the product of the present comparative embodiment.

The detection steps of the degree of cross-linking and the ratio of enzyme degradation for cross-linked collagen of the present comparative example were the same as those of test example 1. The result of the present comparative example is shown in table 1. The productivity of the cross-linked collagen of the present comparative example was 30%, the degree of cross-linking was 50%, the melting point was 62° C., and the ratio of enzyme degradation was 20%. Therefore, the productivity, the degree of cross-linking, the melting point, and the ratio of enzyme degradation of the cross-linked collagen prepared by the present comparative example were not as excellent as the examples 1 to 3.

Comparative Example 4

4-1 Preparation of the Recombinant Collagen Fibers

The collagen fibers were extracted from pigskin to obtain a swine collagen fiber solution. The collagen solution and a phosphate buffer (0.2 M, pH 11.2) were mixed and stirred slowly at 25° C. for 6 hours to perform the recombination reaction of the collagen fibers. In the recombination reaction, the volume ratio of the collagen solution and the phosphate buffer is 9:1. After the recombination reaction of the collagen fibers was finished, the recombinant collagen fibers were collected by centrifugation. Finally, the recombinant collagen fibers were suspended in a MES buffer (0.1 M, pH 5.5) to obtain the recombinant collagen fibers solution (2.7 mg/ml).

4-2 Preparation of First Cross-Linked Fibers

The first cross-linking agent used in the present example comprised 1-ethyl-3-(3 dimethylaminopropyl)carbodiimide hydrochloride (EDC), which was the imine cross-linking agent. In addition, the first cross-linking agent further comprised N-hydroxysuccinimide (NHS) to form a mixture of the first cross-linking agent (EDC/NHS), which was the first cross-linking agent of the present example. In the first cross-linking agent, the molar ratio of EDC and NHS was 5:1.

The first cross-linking agent (EDC/NHS) and the recombinant collagen fibers solution (2.7 mg/ml) were mixed and stirred slowly at 40° C., pH 5.5, for 16 hours to perform the first cross-linking reaction, in which the inter- and intra-molecular amino group and carboxylic group of collagen fibers were cross-linked with each other. In the first cross-linking reaction, the final volume percentage concentration of EDC was 1%. After the first cross-linking reaction was finished, the first cross-linked collagen fibers were collected by centrifugation.

The collected first cross-linked collagen fibers were added to glycine solution (0.1 M) and stirred slowly for 6 hours, in which the volume of the glycine solution was 10 times the volume of the triple cross-linked collagen fibers. Then, the first cross-linked collagen fibers were collected again by centrifugation.

After the collection, the first cross-linked collagen fibers were washed three times by a phosphate buffer (pH 7), in which the volume of the phosphate buffer was 10 times the volume of the first cross-linked collagen fibers. Finally, the first cross-linked collagen fibers were collected by centrifugation to obtain the product of the present comparative embodiment.

The detection steps of the degree of cross-linking and the ratio of enzyme degradation for the cross-linked collagen of the present comparative example were the same as those of test example 1. The result of the present comparative example is shown in table 1. The productivity of the cross-linked collagen of the present comparative steps was 72.1%, the degree of cross-linking was 74.44%, the melting point was 78° C., and the ratio of enzyme degradation was 32%. Therefore, the productivity, the degree of cross-linking, the melting point, and the ratio of enzyme degradation of the cross-linked collagen prepared by the present comparative example were not as excellent as the examples 1 to 3.

Comparative Example 5

5-1 Preparation of the Recombinant Collagen Fibers

The steps for preparing the recombinant collagen fibers were the same as the steps of comparative example 1.

5-2 Preparation of the First Cross-Linked Fibers

The steps for preparing the first cross-linked fibers were the same as the steps of comparative example 1.

5-3 Preparation of the Second Cross-Linked Fibers

In the present comparative example, the second cross-linking agent was 1,4-butanediol diglycidyl ether (BDDE), which is the epoxide cross-linking agent. The first cross-linked collagen fibers were suspended in a phosphate buffer (20 mM, pH 4.5) to obtain the first cross-linked collagen solution (2.7 mg/ml). Then, the first cross-linked collagen solution (2.7 mg/ml) and BDDE were mixed and stirred slowly at 40° C., pH 4.5, for 16 hours to perform the second cross-linking reaction, in which the inter- and intra-molecular carboxylic groups of collagen fibers were cross-linked with each other. In the second cross-linking reaction, the final volume percentage concentration of BDDE is 1%. After the second cross-linking reaction was finished, the double cross-linked collagen fibers were collected by centrifugation.

The collected second cross-linked collagen fibers were added to glycine solution (0.1 M) and stirred slowly for 6 hours, in which the volume of the glycine solution was 10 times the volume of the second cross-linked collagen fibers. Then, the second cross-linked collagen fibers were collected again by centrifugation.

After the collection, the second cross-linked collagen fibers were washed three times by a phosphate buffer (pH 7), in which the volume of the phosphate buffer was 10 times the volume of the second cross-linked collagen fibers. Finally, the second cross-linked collagen fibers were collected by centrifugation to obtain the product of the present comparative embodiment.

The detection steps of the degree of cross-linking and the ratio of enzyme degradation for the cross-linked collagen of the present comparative example were the same as test example 1. The result of the present comparative example is shown in table 1. The productivity of the cross-linked collagen in the present comparative example was 90%. However, the degree of cross-linking was 36.94%, the melting point was 68.33° C., and the ratio of enzyme degradation was 17.4%. Therefore, the ratio of enzyme degradation of the cross-linked collagen of the present comparative example was improved. However, the degree of cross-linking, and the melting point were not as excellent as the examples 1 to 3.

Comparative Example 6

6-1 Preparation of the Recombinant Collagen Fibers

The steps for preparing the recombinant collagen fibers were the same as the steps of comparative example 1.

6-2 Preparation of the First Cross-Linked Fibers

The steps for preparing the first cross-linking reaction were the same as the steps of comparative example 1. Finally, the first cross-linked collagen fibers were suspended in the in a MES buffer (0.1 M, pH 5.5) to obtain the first cross-linked collagen solution (2.7 mg/ml).

6-3 Preparation of the Second Cross-Linked Fibers

The second cross-linking agent used in the present comparative example comprised 1-ethyl-3-(3 dimethylaminopropyl)carbodiimide hydrochloride (EDC), which was the imine cross-linking agent. In addition, the second cross-linking agent further comprised N-hydroxysuccinimide (NHS) to form a mixture of the second cross-linking agent (EDC/NHS), which was the second cross-linking agent of the present example. In the second cross-linking agent, the molar ratio of EDC and NHS was 5:1.

The second cross-linking agent (EDC/NHS) and the first cross-linked collagen solution (2.7 mg/ml) were mixed and stirred slowly at 40° C., pH 5.5, for 16 hours to perform the second cross-linking reaction, in which the inter- and intra-molecular amino group and carboxylic group of collagen fibers were cross-linked with each other. In the second cross-linking reaction, the final volume percentage concentration of EDC was 1%. After the second cross-linking reaction was finished, the double cross-linked collagen fibers were collected by centrifugation to obtain the product of the present example.

The collected second cross-linked collagen fibers were added to glycine solution (0.1 M) and stirred slowly for 6 hours, in which the volume of the glycine solution was 10 times the volume of the second cross-linked collagen fibers. Then, the second cross-linked collagen fibers were collected again by centrifugation.

After the collection, the second cross-linked collagen fibers were washed three times by a phosphate buffer (pH 7), in which the volume of the phosphate buffer was 10 times the volume of the second cross-linked collagen fibers. Finally, the second cross-linked collagen fibers were collected by centrifugation to obtain the product of the present comparative embodiment.

The detection steps of the degree of cross-linking and the ratio of enzyme degradation for the cross-linked collagen of the present comparative example were the same as test example 1. The result of the present comparative example is shown in table 1. The productivity of the cross-linked collagen of the present comparative example was 78.7%, and the degree of cross-linking was 76.74%. However, the melting point was 82.57° C., and the ratio of enzyme degradation was 22%. Therefore, the melting point and the degree of cross-linking of the cross-linked collagen of the present comparative example were improved. However, the productivity and the ratio of enzyme degradation of the cross-linked collagen of the present comparative example were not as excellent as the examples 1 to 3.

Comparative Example 7

7-1 Preparation of the Recombinant Collagen Fibers

The steps for preparing the recombinant collagen fibers were the same as the steps of comparative example 1.

7-2 Preparation of the First Cross-Linked Fibers

The steps for preparing the first cross-linked collagen fibers were the same as the steps of comparative example 1. Finally, the first cross-linked collagen fibers were suspended in a phosphate buffer (20 mM, pH 9.5) to obtain the first cross-linked collagen solution (2.7 mg/ml).

7-3 Preparation of the Second Cross-Linked Fibers

In the present comparative example, the second cross-linking agent was 1,4-butanediol diglycidyl ether (BDDE), which is the epoxide cross-linking agent. The first cross-linked collagen solution (2.7 mg/ml) and BDDE were mixed and stirred slowly at 40° C., pH 9.5, for 16 hours to perform the second cross-linking reaction, in which the inter- and intra-molecular amino groups of collagen fibers were cross-linked with each other. In the second cross-linking reaction, the final volume percentage concentration of BDDE is 1%. After the second cross-linking reaction was finished, the double cross-linked collagen fibers were collected by centrifugation.

The collected second cross-linked collagen fibers were added to glycine solution (0.1 M) and stirred slowly for 6 hours, in which the volume of the glycine solution was 10 times the volume of the second cross-linked collagen fibers. Then, the second cross-linked collagen fibers were collected again by centrifugation.

After the collection, the second cross-linked collagen fibers were washed three times by a phosphate buffer (pH 7), in which the volume of the phosphate buffer was with 10 times the volume of the second cross-linked collagen fibers. Finally, the second cross-linked collagen fibers were collected by centrifugation to obtain the product of the present comparative embodiment.

The detection steps of the degree of cross-linking and the ratio of enzyme degradation for the cross-linked collagen of the present comparative example were the same as test example 1. The result of the present comparative example is shown in table 1 and FIG. 2, which is a perspective view showing the structure of a double cross-linked collagen according to the present comparative example. The productivity of the cross-linked collagen of the present comparative example was 80%, the degree of cross-linking was 71%, the melting point was 73° C., and the ratio of enzyme degradation was 15.3%. The productivity of the cross-linked collagen of the present comparative example was improved. However, the degree of cross-linking, the melting point, and the ratio of enzyme degradation of the cross-linked collagen of the present comparative example were not as excellent as the examples 1 to 3.

TABLE 1

|  | Productivity (%) | Degree of cross-linking (%) | Melting point (° C.) | Ratio of enzyme degradation (%) | Remarks |
|---|---|---|---|---|---|
| Example 1 | 83 | 75.62 | 82.18 | 9.17 | GA/BDDE (acidic environment)/EDC |
| Example 2 | 77 | 76.61 | 84.53 | 8.34 | GA/EDC/BDDE (acidic environment) |
| Example 3 | 73.8 | 76.43 | 81.75 | 8.11 | EDC/GA/BDDE (acidic environment) |

TABLE 1-continued

| | Productivity (%) | Degree of cross-linking (%) | Melting point (° C.) | Ratio of enzyme degradation (%) | Remarks |
|---|---|---|---|---|---|
| Comparative example 1 | 91.2 | 32.88 | 68.33 | 100 | GA |
| Comparative example 2 | 38.5 | 8.5 | 50.33 | 34 | BDDE (acidic environment) |
| Comparative example 3 | 30 | 50 | 62 | 20 | BDDE (alkaline environment) |
| Comparative example 4 | 72.1 | 74.44 | 78 | 32 | EDC |
| Comparative example 5 | 90 | 36.94 | 68.36 | 17.4 | GA/BDDE (acidic environment) |
| Comparative example 6 | 78.7 | 76.74 | 82.57 | 22 | GA/EDC |
| Comparative example 7 | 80 | 71 | 73 | 15.3 | GA/BDDE (alkaline environment) |

Figure 2:
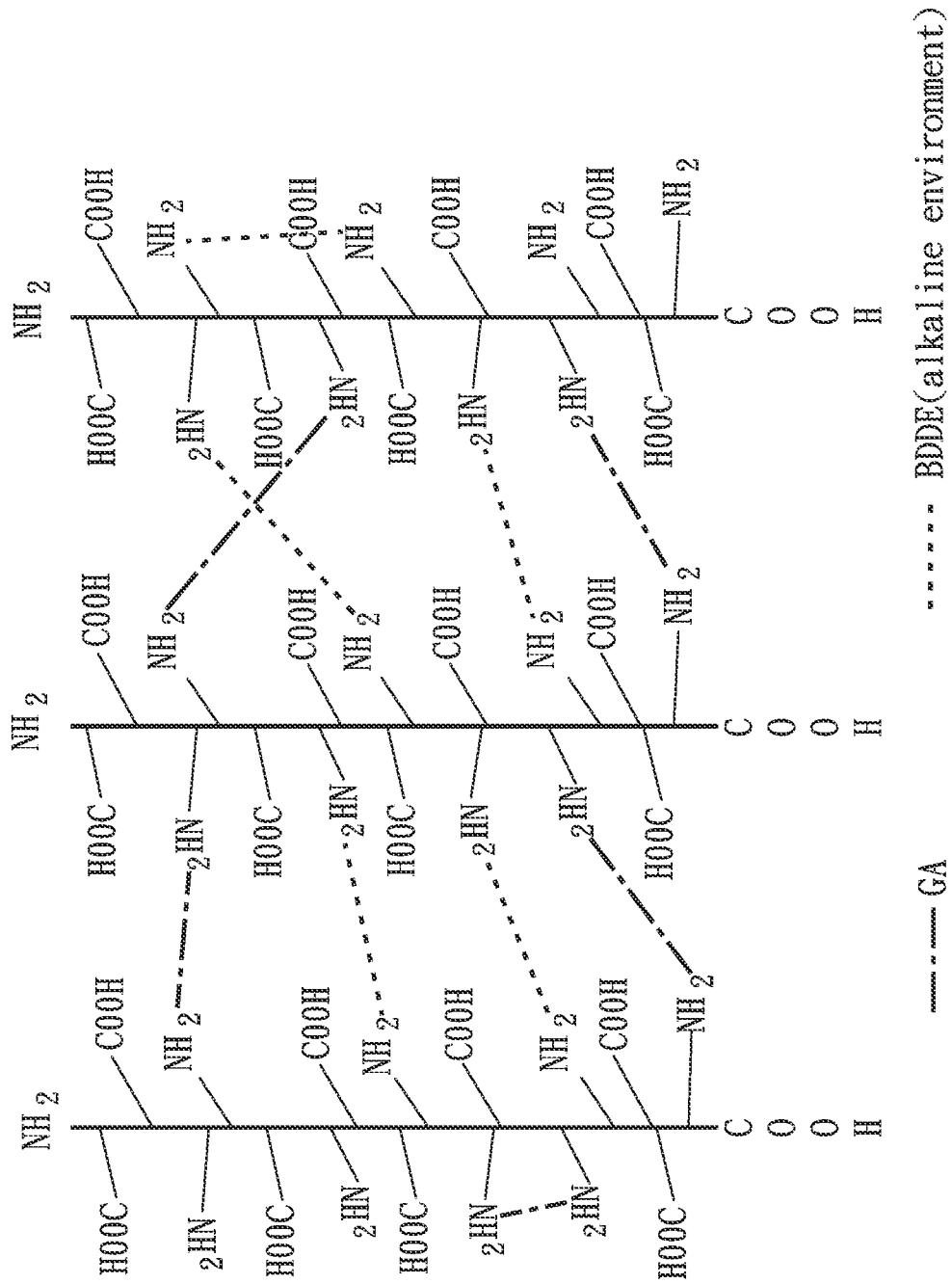
FIG. 2 is a perspective view showing the structure of a double cross-linked collagen according to Comparative example 7.

According to the result of table 1, FIGS. 1 to 3, and the description illustrated above, the triple cross-linked collagen manufactured by the method of the present invention has good productivity and enough inter- and intra-molecular cross-linking reaction between amino groups, amino group and carboxylic group, and carboxylic groups of the collagen. In addition, comparing with the comparative examples, the degree of cross-linking and the melting point of the triple cross-linked collagen were also improved. Furthermore, the ratio of enzyme degradation was obviously lower than the comparative examples. Therefore, the triple cross-linked collagen manufactured by the method of the present invention has better stability than the first cross-linked collagen and the double cross-linked collagen of the comparative examples. For this reason, the triple cross-linked collagen is more suitable to apply in dentistry, orthopedics, neurosurgery, plastic surgery, or as a pharmaceutical carrier than the first cross-linked collagen and the double cross-linked collagen, which were manufactured by the method of the prior art.

Although the present invention has been explained in relation to its preferred embodiment, it is to be understood that many other possible modifications and variations can be made without departing from the spirit and scope of the invention as hereinafter claimed.

What is claimed is:

1. A method for manufacturing a triple cross-linked collagen, comprising the following steps:
providing a soluble collagen sample;
mixing the collagen sample with a first cross-linking agent to form a first cross-linked collagen, wherein the first cross-linking agent is one selected from the group consisting of an aldehyde cross-linking agent, and an imine cross-linking agent;
mixing the first cross-linked collagen with a second cross-linking agent to form a second cross-linked collagen, wherein the second cross-linking agent is one selected from the group consisting of an aldehyde cross-linking agent, and an imine cross-linking agent, and the second cross-linking agent is different from the first cross-linking agent; and
mixing the second cross-linked collagen with a third cross-linking agent to form a triple cross-linked collagen, wherein the third cross-linking agent is an epoxide cross-linking agent;
wherein the cross-linking reaction for the epoxide cross-linking agent proceeds at pH 3 to pH 5 and 30° C. to 50° C.

2. The method as claimed in claim 1, further comprising a step after forming the triple cross-linked collagen:
mixing the triple cross-linked collagen with an excessive glycine solution, and washing the triple cross-linked collagen by a phosphoric acid buffer solution to neutralize the triple cross-linked collagen.

3. The method as claimed in claim 1, wherein the collagen sample comprises a collagen fiber, and the collagen sample is at least one selected from the group consisting of bovine collagen, swine collagen, sheep collagen, horse collagen, fish collagen, and human collagen.

4. The method as claimed in claim 1, wherein the collagen sample is at least one selected from the group consisting of type I collagen, type II collagen, type III collagen, type IV collagen, and type V collagen.

5. The method as claimed in claim 3, wherein the collagen sample is type I collagen.

6. The method as claimed in claim 1, wherein the collagen sample comprises a recombinant collagen fiber.

7. The method as claimed in claim 1, wherein the aldehyde cross-linking agent is at least one selected from the group consisting of formaldehyde, glyoxal, and glutaraldehyde.

8. The method as claimed in claim 1, wherein the aldehyde cross-linking agent is glutaraldehyde.

9. The method as claimed in claim 7, wherein the aldehyde cross-linking agent proceeds a cross-linking reaction in pH 6 to pH 9 and 20° C. to 50° C.

10. The method as claimed in claim 7, wherein the concentration of the aldehyde cross-linking agent is 15 ppm to 70 ppm.

11. The method as claimed in claim 1, wherein the imine cross-linking agent is at least one selected from the group consisting of 1-ethyl-3-(3-dimethylaminopropyl)carbodiimide hydrochloride (EDC), 1-Cyclohexyl-3-(2-morpholinoethyl)carbodiimide (CMC), dicyclohexyl carbodiimide (DCC), and diisopropyl carbodiimide (DIC).

12. The method as claimed in claim 1, wherein the imine cross-linking agent is 1-ethyl-3-(3dimethylaminopropyl)carbodiimide hydrochloride (EDC).

13. The method as claimed in claim 12, wherein the imine cross-linking agent further comprises N-hydroxysuccinimide (NHS) to form a mixture of imine cross-linking agent.

14. The method as claimed in claim 11, wherein the imine cross-linking agent proceeds the cross-linking reaction in pH 4 to pH 6 and 30° C. to 50° C.

15. The method as claimed in claim 11, wherein a volume percentage concentration for the imine cross-linking agent is 1% to 4%.

16. The method as claimed in claim 1, wherein the epoxide cross-linking agent is at least one selected from the group consisting of 1,4-butanediol diglycidyl ether (BDDE), ethylene glycol diglycidyl ether (EGDGE), glycerol polyglycidyl ether, and diglycerol polyglycidyl ether.

17. The method as claimed in claim 1, wherein the epoxide cross-linking agent is 1,4-butanediol diglycidyl ether (BDDE).

18. The method as claimed in claim 16, wherein the volume percentage concentration for the epoxide cross-linking agent is 0.5% to 4%.

19. The method as claimed in claim 1, wherein the first cross-linking agent is an aldehyde cross-linking agent.

20. The method as claimed in claim 1, wherein the function of the first cross-linking agent is to proceeding cross-linking reaction to form covalent bonds between amino functional groups.

* * * * *